United States Patent [19]

Krauss

[11] Patent Number: 5,008,396
[45] Date of Patent: Apr. 16, 1991

[54] PROCESS FOR THE PREPARATION OF 5-AMINO-3-CHLOROSULFONYL-1,2,4-TRIAZOLE

[75] Inventor: Richard C. Krauss, Midland, Mich.

[73] Assignee: DowElanco, Indianapolis, Ind.

[21] Appl. No.: 432,289

[22] Filed: Nov. 6, 1989

[51] Int. Cl.$^5$ .............................................. C07D 249/12
[52] U.S. Cl. .................................................. 548/263.8
[58] Field of Search ...................................... 548/263.8

[56] References Cited

U.S. PATENT DOCUMENTS

| | | | |
|---|---|---|---|
| 4,734,123 | 3/1988 | Monte | 71/92 |
| 4,755,212 | 7/1988 | Kleschick et al. | 71/92 |
| 4,889,553 | 12/1989 | Rowson et al. | 71/92 |

OTHER PUBLICATIONS

March, "Advanced Organic Chemistry Reactions, Mechanisms and Structure" 2nd ed. (1977) pp. 1110–1111, 1115.

*Primary Examiner*—Richard L. Raymond
*Assistant Examiner*—Patricia L. Morris
*Attorney, Agent, or Firm*—Craig E. Mixan; Ronald G. Brookens

[57] ABSTRACT

5-Amino-3-chlorosulfonyl-1,2,4-triazole is prepared by the chlor-oxidation of 5-amino-3-mercapto-1,2,4-triazole. The process is characterized by the preformation of disulfide from the mercaptan prior to treatment with chlorine. The 5-amino-3-chlorosulfonyl-1,2,4-triazole reaction mixture can be directly reacted with substituted anilines to prepare N-(3-(((aryl)amino)sulfonyl)-1H-1,2,4-triazol-5-yl)amines which are useful intermediates for the manufacture of herbicides.

10 Claims, No Drawings

PROCESS FOR THE PREPARATION OF 5-AMINO-3-CHLOROSULFONYL-1,2,4-TRIAZOLE

FIELD OF THE INVENTION

The present invention is directed to a process for the preparation of 5-amino-3-chlorosulfonyl-1,2,4-triazole by the chlor-oxidation of 5-amino-3-mercapto-1,2,4-triazole. More particularly, the present invention is directed to a process for accomplishing this conversion which is characterized by the preformation of the corresponding disulfide prior to treatment with chlorine.

BACKGROUND OF THE INVENTION

Many N-(3-(((aryl)amino)sulfonyl)-1H-1,2,4-triazol-5-yl)amines (I),

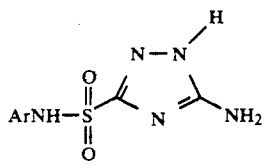

their preparation, and their value as intermediates in the manufacture of substituted 1,2,4-triazolo[1,5-a]pyrimidine-2-sulfonanilide herbicides (II)

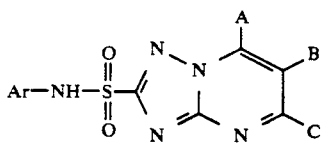

have been described in U.S. Pat. Nos. 4,734,123 and 4,755,212. Recently, the direct preparation of N-(3-(((aryl)amino)sulfonyl)-1H-1,2,4-triazol-5-yl)amines (I) from substituted anilines and from 5-amino-3-chlorosulfonyl-1,2,4-triazole (III) has been reported.

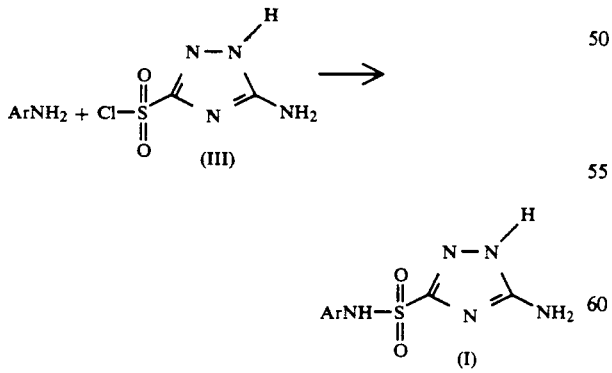

The 5-amino-3-chlorosulfonyl-1,2,4-triazole (III) is obtained by treating 5-amino-3-mercapto-1,2,4-triazole (IV) with chlorine in an aqueous acid medium until the reaction is substantially complete.

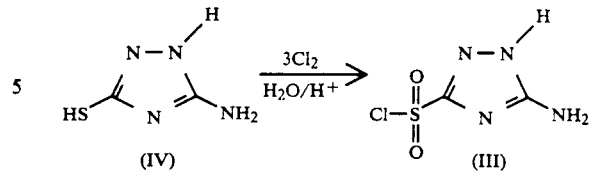

Although the direct chlor-oxidation of 5-amino-3-mercapto-1,2,4-triazole to 5-amino-3-chlorosulfonyl-1,2,4-triazole occurs in relatively good yield, the process is plagued by mixing problems associated with intractable slurries which complicate scale-up both with respect to chlorine dispersion and to heat transfer. In addition, the product is contaminated with 3-amino-1,2,4-triazole (V)

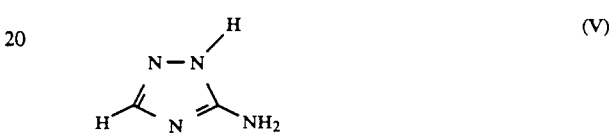

as a major by-product of the chlor-oxidation process. The discovery of an improved process which would alleviate the mixing difficulties associated with the intractable slurries and which would eliminate the formation of the major contaminant would be highly desirable.

SUMMARY OF THE INVENTION

The present invention relates to a process for preparing 5-amino-3-chlorosulfonyl-1,2,4-triazole

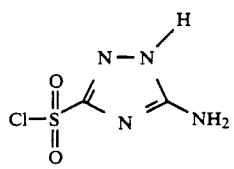

from 5-amino-3-mercapto-1,2,4-triazole

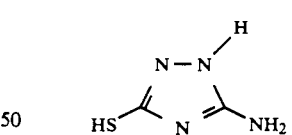

in an aqueous acid medium which comprises the consecutive steps of:

(a) contacting the 5-amino-3-mercapto-1,2,4-triazole with an oxidizing agent to convert it to the corresponding disulfide

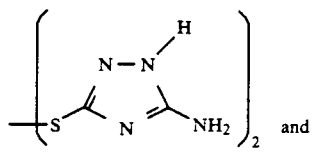 and (b) contacting the disulfide with chlorine.

The disulfide may be preformed from the 5-amino-3-mercapto-1,2,4-triazole or may be prepared in situ prior to chlorination. Preferably, the two steps are conducted without isolation of the intermediate disulfide.

One preferred method for quantitatively converting 5-amino-3-mercapto-1,2,4-triazole to the corresponding disulfide is oxidation with hydrogen peroxide. By preforming the disulfide prior to treatment with chlorine, the 3-amino-1,2,4-triazole contaminant can be avoided.

In addition, the 5-amino-3-chlorosulfonyl-1,2,4-triazole reaction mixture can be directly reacted with substituted anilines to prepare intermediates useful for the manufacture of herbicides.

DETAILED DESCRIPTION OF THE INVENTION

During the direct chlorination of 5-amino-3-mercapto-1,2,4-triazole, 3-amino-1,2,4-triazole is observed as the major by-product. The appearance of this highly reduced compound in an oxidation reaction is somewhat surprising. It has now been found that 2 equivalents of 5-amino-3-mercapto-1,2,4-triazole react with 5-amino-3-chlorosulfonyl-1,2,4-triazole under the reaction conditions to produce 3-amino-1,2,4-triazole and the $SO_2$ complex of the disulfide of the mercaptotriazole.

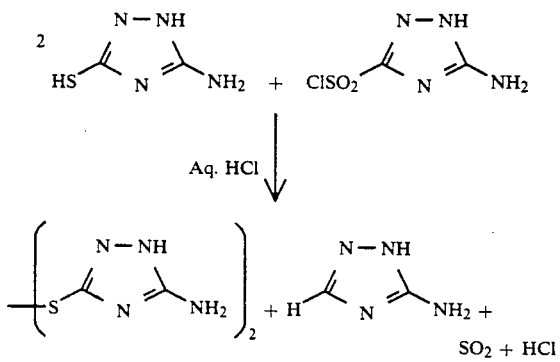

By converting all of the 5-amino-3-mercapto-1,2,4-triazole to disulfide prior to treatment with chlorine, the product chlorosulfonyltriazole is never coexistent with the starting mercaptotriazole and the formation of the by-product 3-amino-1,2,4-triazole is precluded.

The disulfide may be preformed or may be prepared in situ from 5-amino-3-mercapto-1,2,4-triazole. The conversion of the mercaptan to the disulfide is readily accomplished with mild oxidizing agents and is most conveniently performed in situ. Many diverse oxidizing agents can convert thiols to disulfides, including, for example, iodine, potassium ferricyanide, thallic trifluoroacetate, azobis(N,N-dimethylformamide) and even, in some circumstances, just air in the presence of base, but hydrogen peroxide under acidic conditions is generally preferred. Hydrogen peroxide concentrations of from 3 to 70 percent can be employed. In general, hydrogen peroxide concentrations of 10 to 50 percent are preferred. The use of 30 percent hydrogen peroxide is most preferred. Strong oxidants, which effectively oxidize sulfur compounds completely to the corresponding sulfonic acids, should be avoided.

The conversion of the mercaptan to the disulfide is quantitative with 0.5 equivalents of peroxide. Since peroxide is readily decomposed by chlorine, the use of excess peroxide presents no problems beyond upsetting the stoichiometry with respect to subsequent chlorination.

$$H_2O_2 + Cl_2 \rightarrow O_2 + 2HCl$$

Aqueous acid is generally employed as the initial reaction medium. Since the subsequent chlorination generates hydrochloric acid, aqueous hydrochloric acid is the preferred reaction medium. To keep the reaction slurry more tractable, the initial oxidation is carried out in aqueous HCl of a concentration between about 15 and about 30 weight percent. The use of constant boiling (6.25N) HCl has been found to be quite suitable for this purpose. An amount of aqueous acid containing medium is generally employed so that the concentration of 5-amino-3-mercapto-1,2,4-triazole (or the corresponding disulfide) is about 5 to about 30 weight percent of the total reaction mixture.

Because the reaction mixture is a slurry, agitation is important to promote contact of the reagents.

The temperature is generally maintained in the range of about the freezing point of the mixture to about 70° C. It is preferably maintained from about 30° to about 50° C.

After conversion of the mercaptotriazole to the disulfide is complete, the addition of chlorine is commenced. Again, agitation is important to promote contact of the reactants.

The temperature is generally maintained in the range of about the freezing point of the mixture to about 50° C. It is preferably maintained at about −10° to about 30° C. and more preferably at about −5° to about 25° C. External cooling is generally employed as the reaction is exothermic.

The reaction theoretically requires 2.5 moles of chlorine per mole of disulfide. Since any excess peroxide present from the in situ preparation of the disulfide consumes chlorine, allowance must be made for providing sufficient chlorine to both decompose the peroxide and to oxidize the disulfide to the desired chlorosulfonyltriazole. Slight excesses of from 2 to 5 percent are often employed. Chlorine is usually added until uptake virtually ceases, since the reaction generally takes place about as fast as the chlorine can be added.

Since the reaction generates hydrochloric acid and since the hydrochloride salt of the product, 5-amino-3-chlorosulfonyl-1,2,4-triazole forms an extremely thick slurry at high acid concentrations, it is beneficial to add water during the latter stages of the oxidation so as to finish the reaction at an acid concentration in the range of 20-30 weight percent HCl.

In a typical reaction, 5-amino-3-mercapto-1,2,4-triazole, either sieved or milled to promote a free flowing slurry, and 6.25N (constant boiling) HCl are charged to a reaction vessel and vigorously agitated. Addition of 0.5 equivalents of 30 percent $H_2O_2$ at about 50° C. and at a rate consistent with heat removal produces the disulfide quantitatively and nearly instantaneously. Upon completion of the peroxide addition, the flowable slurry of the disulfide is cooled below 5° C. Chlorine is sparged into the reaction at a rate consistent with heat removal and water is con-added so as to maintain the HCl concentration at approximately 6N. The end of the chlorination is determined by monitoring the disappearance of the disulfide and generally requires 2-5 mole percent $Cl_2$ in excess of the theoretical.

The 5-amino-3-chlorosulfonyl-1,2,4-triazole can be recovered as a wet solid containing some hydrochloric acid by conventional means, such as by filtration or centrifugation. It is best recovered quickly after chlorine addition is complete and then used quickly as is or dried in order to avoid yield losses due to hydrolysis or sulfur dioxide evolution.

Alternatively and preferably, the reaction mixture can be directly coupled with a substituted aniline to prepare N-(3-(((aryl)amino)sulfonyl)-1H-1,2,4-triazol-5-yl) amines. Suitable substituted anilines are described in U.S. Pat. Nos. 4,734,123 and 4,755,212. Preferred anilines are of the formula

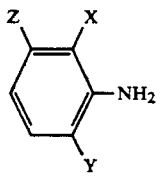

wherein
X represents F, Cl, Br or $C_1$-$C_4$ alkyl,
Y represents F, Cl, Br or $NO_2$, and
Z represents H, $C_1$-$C_4$ alkyl or $C_1$-$C_4$ alkoxy.

Before proceeding with the coupling reaction, any residual oxidizer is destroyed by the addition of, for example, $Na_2S_2O_5$, $NaHSO_3$ or $SO_2$. The use of a reducing agent at this point protects the substituted aniline from oxidative decomposition.

Since protonated anilines do not react, an external base must be provided to neutralize the HCl present in the chlorosulfonyltriazole reaction mixture and to neutralize the additional equivalent of HCl produced in the coupling reaction. Suitable HCl acceptors include, for example, inorganic bases such as the alkali metal hydroxides or organic bases such as trialkyl amines. It is often convenient to employ an excess of the substitited aniline as the base. High yields of coupled product can be obtained by using at least enough substituted aniline (a) to react, (b) to neutralize the HCl initially present in the chlorosulfonyltriazole reaction mixture, and (c) to neutralize the additional equivalent of HCl produced in the coupling reaction. 2,6-Difluoroaniline is the most preferred aniline for this embodiment.

In a typical reaction, the 5-amino-3-chlorosulfonyl-1,2,4-triazole reaction mixture, previously treated with reducing agent, is rapidly added with good stirring to 12 equivalents of substituted aniline. The reaction proceeds rapidly and is usually complete in about 30 minutes (min). Excess substituted aniline can be recovered by treating with caustic to liberate the free aniline which can then be recovered by conventional techniques, such as, for example, steam distillation and/or decantation. The coupled product is then recovered by conventional procedures.

The following examples are presented to illustrate the invention and should not be construed as limiting the scope of the invention. All melting points are uncorrected.

High pressure liquid chromatography (HPLC) analyses were conducted on a chromatograph composed of an Hitachi L6200 pump, Kratos Spectroflow 757 variable wavelength detector at 214 nm, Spectra Physics SP 4290 integrator and Rheodyne 7125 injector with a 20 $\mu$l sample loop and a Jones Chromatography (Littleton Co.) Apex Octyl 5$\mu$, 25 cm$\times$4.6 mm reverse phase column. The column was eluted at 1.8 cc/min. with 8 volume percent acetonitrile and 0.1 volume percent $H_3PO_4$ in water.

EXAMPLE I

Preparation of Di-(5-amino-1,2,4-triazol-3-yl)disulfide

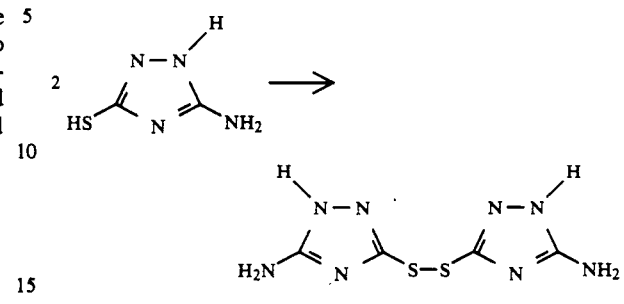

3-Amino-5-mercapto-1,2,4-triazole (46.5 grams (g); 0.4 moles) was suspended in 320 cc of 6.25N HCl. A solution of 23 g (0.203 moles) of 30 percent $H_2O_2$ in 60 cc of deionized water was added over 30 min while maintaining the temperature between 25° and 30° C. The resulting white slurry was cooled to 10° C. and vacuum filtered. The filter cake was washed with 300 cc of acetone and dried to yield 53 g (87.5 percent yield) of the dihydrochloride salt of the titled disulfide. The product was 99.8 percent pure (area percent HPLC). The free di-(5-amino-1,2,4-triazol-3-yl)disulfide, obtained by reslurrying the dihydrochloride in water and by carefully neutralizing with $Na_2CO_3$. melted at 250°–256° C. with decomposition.

EXAMPLE II

Preparation of 5-Amino-3-Chlorosulfonyl-1,2,4-Triazole (III) and its Coupling with 2,6-Difluoroaniline

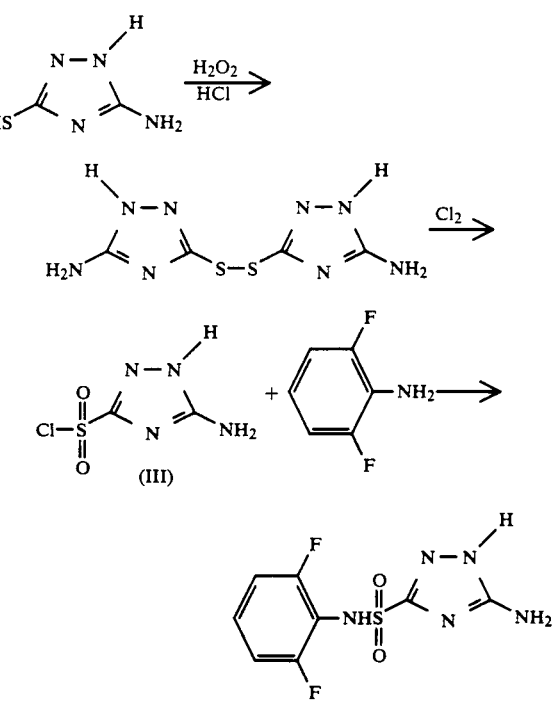

To a 1 liter, 3-necked flask, equipped with dropping funnel, mechanical stirrer and chlorine sparge tube, was added 59 g (0.5 moles) of 3-amino-5-mercapto-1,2,4-triazole and 400 cc of 6.25N HCl. While maintaining the reaction temperature between 20° and 30° C. using an ice/water bath, 30 g (0.26 moles) of 30 percent H₂O₂ were added dropwise over 20 min. Complete conversion to the disulfide was confirmed by HPLC and the reaction was cooled to 0° C. with an ice/ethanol bath. Chlorine (94.8 g) was sparged into the cold reaction over 2 hours (hrs) and 2×100 cc portions of deionized water were added at intervals after 24 g and 42 g of chlorine had been added. Complete conversion was confirmed by HPLC analysis and then 10 g of Na₂S₂O₅ were added to destroy any excess chlorine.

The thin slurry of 5-amino-3-chlorosulfonyl-1,2,4-triazole was added all at once to 783.4 g of freshly distilled 2,6-difluoroaniline in a 2 liter 3-necked flask equipped with a mechanical agitator. After addition was complete, the chlorosulfonyltriazole flask was washed with 200 cc of deionized water and the wash was added to the reaetion. The coupling reaction exothermed to 36° C. After 20 min the reaction was found to be complete by HPLC. The reaction was neutralized with 500 g of 50 percent NaOH (pH 12.0) and the mixture was cooled to about 30° C. and filtered through a glass frit to improve the interface between liquid phases. The filtrate was transferred to a separatory funnel and the bottom layer of 2,6-difluoroaniline (697 g) was decanted. The aqueous phase was washed with 100 cc of methylene chloride to remove any additional aniline. The aqueous solution was returned to the reaction flask and heated to 90° C. Acetic acid (100 g) was added dropwise to precipitate the product (pH 4.3). The slurry was cooled over several hrs to 45° C. and then rapidly to 5° C. The slurry was vacuum filtered and the filter cake was washed with 200 cc of ice water. After drying at 85° C. under vacuum, 118.3 g of N-(3-(((2,6-difluorophenyl)amino)sulfonyl)-1H-1,2,4-triazol-5-yl)amine (96 percent pure) was collected giving an overall yield of 87 percent based on 5-amino-3-mercapto-1,2,4-triazole. The proton and carbon nmr spectra were consistent with the structure.

EXAMPLE III

Preparation of 5-Amino-3-Chlorosulfonyl-1,2,4-Triazole and its Coupling with 2,6-Difluoroaniline 5-Amino-3-mercapto-1,2,4-triazole (23.5 g; 0.2 moles) and 160 cc of 6.25N HCl (1.0 mole) were charged to a 500 cc 3-necked flask equipped with mechanical stirrer, dropping funnel and chlorine sparge tube. While maintaining the reaction temperature between 20° and 30° C., 12 g (0.105 moles) of 30 percent H₂O₂ were added dropwise over 10 min. Following the addition, the reaction was briefly warmed to 50° C. and then cooled to 0° C. using an ice/ethanol bath. Chlorine (39 g; 0.56 moles) was sparged into the reaction over 2 hrs at 0° C. and 60 cc of deionized water were added near the end of the reaction to maintain a stirrable slurry. After confirming complete conversion to the sulfonyl chloride by HPLC, 3 g of Na₂S₂O₅ were added to reduce any excess chlorine.

The 5-amino-3-chlorosulfonyl-1,2,4-triazole reaction mixture was added all at once to 310 g (2.4 moles) of wet 2,6-difluoroaniline and the reaction exothermed to about 45° C. Coupling was complete after 20 min. The reaction was neutralized with 176 g (2.2 moles) of 50 percent NaOH to give a pH of 6.0. 2,6-Difluoroaniline was recovered by steam distillation using a Dean-Stark trap as receiver allowing the aqueous phase of the distillate to continuously return to the pot. After 283.5 g of 2,6-difluoroaniline were recovered, the resulting slurry contained N-(3-(((2,6-difluorophenyl)amino)sulfonyl)-1H-1,2,4-triazol-5-yl)amine with only a trace of the aniline remaining.

What is claimed is:

1. A process for preparing 5-amino-3-chlorosulfonyl-1,2,4-triazole

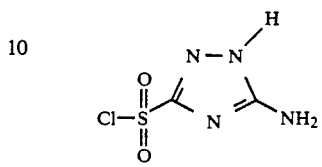

from 5-amino-3-mercapto-1,2,4-triazole

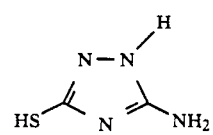

in an aqueous acid medium which comprises the consecutive steps of:
   (a) contacting the 5-amino-3-mercapto-1,2,4-triazole with an oxidizing agent to convert it to the corresponding disulfide

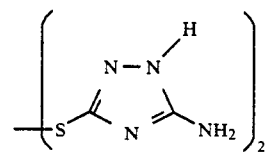

(b) contacting the disulfide with chlorine.

2. The process of claim 1 in which the 5-amino-3-mercapto-1,2,4-triazole is converted to the disulfide by oxidation with hydrogen peroxide.

3. The process of claim 2 in which the two steps are conducted without isolation of the intermediate disulfide.

4. The process of claim 2 in which 10 to 50 percent hydrogen peroxide is employed.

5. The process of claim 2 in which the initial concentration of hydrochloric acid in the aqueous reaction medium is between about 15 and about 30 weight percent.

6. The process of claim 5 in which the final concentration of hydrochloric acid is maintained between about 20 and about 30 weight percent.

7. The process of claim 2 which comprises the additional step of preparing an N-(3-(((aryl)amino)sulfonyl)-1H-1,2,4-triazol-5-yl)amine of the formula

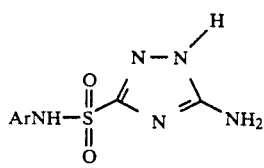

wherein Ar is a substituted phenyl group of the formula

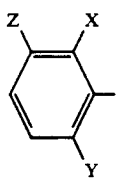

in which

X represents F, Cl, Br or $C_1$-$C_4$ alkyl,

Y represents F, Cl, Br or $NO_2$, and

Z represents H, $C_1$-$C_4$ alkyl or $C_1$-$C_4$ alkoxy, by directly coupling the 5-amino-3-chlorosulfonyl-1,2,4-triazole reaction mixture with a substituted aniline of the formula

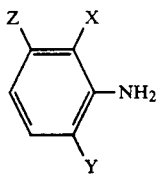

wherein X, Y and Z are as previously defined.

8. The process of claim 7 in which residual oxidizer is destroyed by a reducing agent prior to contacting the substituted aniline.

9. The process of claim 7 in which the substituted aniline is 2,6-difluoroaniline.

10. The process of claim 9 in which enough difluoroaniline is employed to
(a) react with the 5-amino-3-chlorosulfonyl-1,2,4-triazole;
(b) neutralize the HCl present in the 5-amino-3-chlorosulfonyl-1,2,4-triazole reaction mixture; and
(c) neutralize the additional equivalent of HCl produced in the coupling reaction.

* * * * *